(12) United States Patent
Rich et al.

(10) Patent No.: US 9,724,002 B2
(45) Date of Patent: Aug. 8, 2017

(54) METHODS, DEVICES AND SYSTEMS FOR PHOTOPLETHYSMOGRAPHY AT THE NASAL COLUMELLA

(71) Applicants: David Rich, Gainesville, FL (US); Andrew Kersey, Gainesville, FL (US)

(72) Inventors: David Rich, Gainesville, FL (US); Andrew Kersey, Gainesville, FL (US)

( * ) Notice: Subject to any disclaimer, the term of this patent is extended or adjusted under 35 U.S.C. 154(b) by 743 days.

(21) Appl. No.: 14/202,247

(22) Filed: Mar. 10, 2014

(65) Prior Publication Data

US 2014/0275930 A1  Sep. 18, 2014

Related U.S. Application Data

(60) Provisional application No. 61/798,227, filed on Mar. 15, 2013.

(51) Int. Cl.
| | |
|---|---|
| *A61B 5/02* | (2006.01) |
| *A61B 5/024* | (2006.01) |
| *A61B 5/00* | (2006.01) |
| *A61B 5/087* | (2006.01) |
| *A61B 5/1455* | (2006.01) |
| *A61B 5/097* | (2006.01) |

(52) U.S. Cl.
CPC ........ *A61B 5/02427* (2013.01); *A61B 5/0873* (2013.01); *A61B 5/0878* (2013.01); *A61B 5/14552* (2013.01); *A61B 5/6819* (2013.01); *A61B 5/6838* (2013.01); *A61B 5/097* (2013.01); *A61B 5/6832* (2013.01); *A61B 2560/0425* (2013.01); *A61B 2562/164* (2013.01)

(58) Field of Classification Search
CPC ............ A61B 5/02427; A61B 5/02416; A61B 5/0524; A61B 5/14552; A61B 5/6838; A61B 5/6819
See application file for complete search history.

(56) References Cited

U.S. PATENT DOCUMENTS

| | | | |
|---|---|---|---|
| 5,069,222 A | 12/1991 | McDonald | |
| 2002/0029004 A1* | 3/2002 | Starr | A61B 5/087 600/538 |
| 2002/0138017 A1* | 9/2002 | Bui | A61B 5/0002 600/537 |
| 2004/0186390 A1 | 9/2004 | Ross | |
| 2004/0230108 A1* | 11/2004 | Melker | A61B 5/0873 600/340 |
| 2007/0219059 A1 | 9/2007 | Schwartz | |
| 2010/0179438 A1 | 7/2010 | Heneghan | |
| 2010/0192952 A1 | 8/2010 | Melker | |

FOREIGN PATENT DOCUMENTS

| | | |
|---|---|---|
| WO | 2012024106 A2 | 2/2012 |
| WO | 2012032501 A1 | 3/2012 |

OTHER PUBLICATIONS

Foreign search results dated Jul. 2, 2014 for PCT/US/2014/023506.

* cited by examiner

*Primary Examiner* — Christian Jang

(57) ABSTRACT

Provided according to embodiments of the invention are photoplethysmography (PPG) sensors, systems and methods of using the same. In some embodiments of the invention, methods of obtaining a photoplethysmography (PPG) signals include securing a PPG sensor onto a nasal columella of an individual; and obtaining a PPG signal from the PPG sensor.

26 Claims, 4 Drawing Sheets

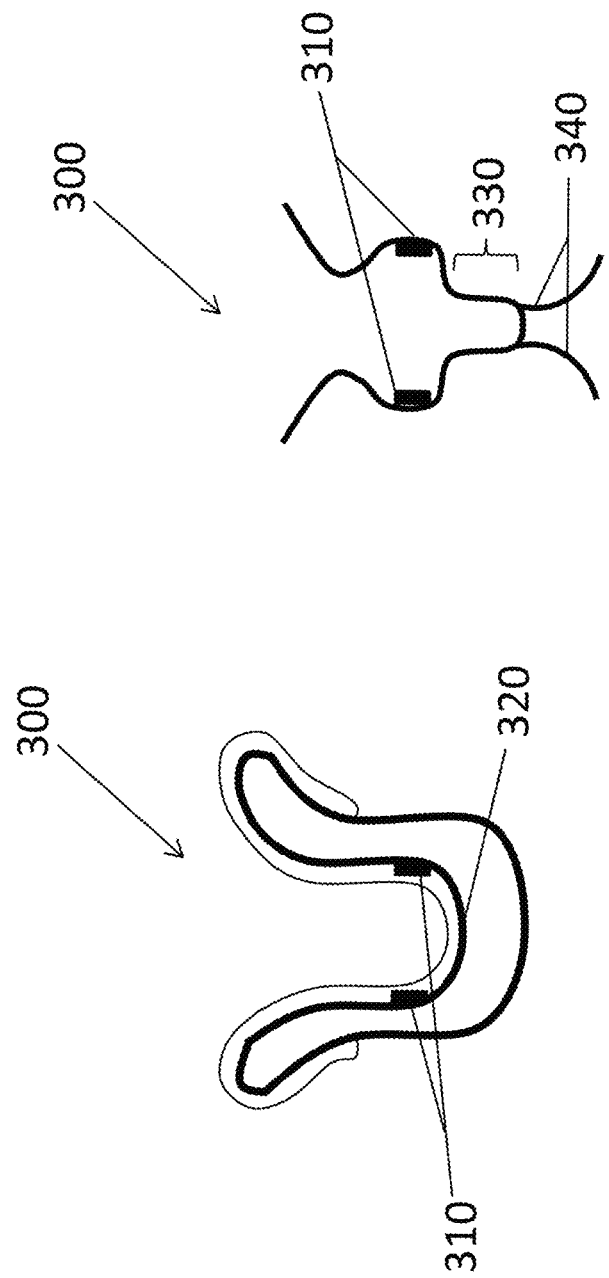

METHODS, DEVICES AND SYSTEMS FOR PHOTOPLETHYSMOGRAPHY AT THE NASAL COLUMELLA

CROSS-REFERENCE TO RELATED APPLICATIONS

This application claims the benefit of U.S. Provisional Application No. 61/798,227, filed Mar. 15, 2013, the contents of which are incorporated herein by reference in their entirety.

FIELD OF THE INVENTION

The present invention relates to biological sensors, and in particular, to photoplethysmography sensors. The present invention also relates to methods, systems and devices for use with photoplethysmography sensors.

BACKGROUND OF THE INVENTION

Photoplethysmography, or "PPG", is an optical technique for detecting blood volume changes in a tissue. In this technique, one or more emitters are used to direct light at a tissue and one or more detectors are used to detect the light that is transmitted through the tissue ("transmissive PPG") or reflected by the tissue ("reflectance PPG"). The volume of blood, or perfusion, of the tissue affects the amount of light that is transmitted or reflected. Thus, the PPG signal varies with changes in the perfusion of the tissue.

The blood volume in a tissue changes with each heartbeat, and so the PPG signal also varies with each heartbeat. Traditionally, this component of the PPG signal is referred to as the "AC component" component of the signal, and is also often referred to as the "pulsatile component." Blood volume is also affected by other physiological processes in the body, including respiration, venous blood volume, sympathetic and parasympathetic tone and certain pathologies. The changes in the PPG signal due to these and other physiological processes, along with changes in the PPG signal due to noise caused by non-physiological processes such as ambient light and bodily movement, have traditionally been referred to collectively as the "DC component."

The present inventors have recently extracted specific parameters from the DC component. Traditional sites for monitoring PPG, such as fingers and toes, generally provide a relatively small PPG signal, and the quality of this signal may be negatively impacted by sympathetic innervation in these tissue sites. Thus, the DC component signal from traditional peripheral sites may not be of sufficient strength and quality to effectively separate out the signals from different physiological processes.

Thus, new devices, systems and methods for PPG monitoring may be desirable.

BRIEF DESCRIPTION OF THE DRAWINGS

The following drawings are provided to illustrate various aspects of the present inventive concept and are not intended to limit the scope of the present invention unless specified herein.

FIG. 2A depicts a clip body having a rounded shape; FIG. 2B depicts a clip body having a squared off shape and first and second end portions of substantially equal length; FIG. 2C depicts a clip body having first and second end portions of different lengths; and FIG. 2D depicts an irregularly shaped clip body.

FIGS. 3A and 3B are cross-sectional illustrations showing additional clip body types for use with the nasal columella.

DETAILED DESCRIPTION OF EMBODIMENTS OF THE INVENTION

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element is referred to as being "on" or "adjacent" to another element, it can be directly on or directly adjacent to the other element or intervening elements may also be present. In contrast, when an element is referred to as being "directly on" or "directly adjacent" to another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers refer to like elements throughout the specification.

It will be understood that, although the terms first, second, etc. may be used herein to describe various elements, these elements should not be limited by these terms. These terms are only used to distinguish one element from another. Thus, a first element discussed below could be termed a second element without departing from the teachings of the present invention.

Embodiments of the present invention are described herein with reference to schematic illustrations of idealized embodiments of the present invention. As such, variations from the shapes of the illustrations as a result, for example, of manufacturing techniques and/or tolerances, are to be expected.

Photoplethysmography Sensors

Figure 1:
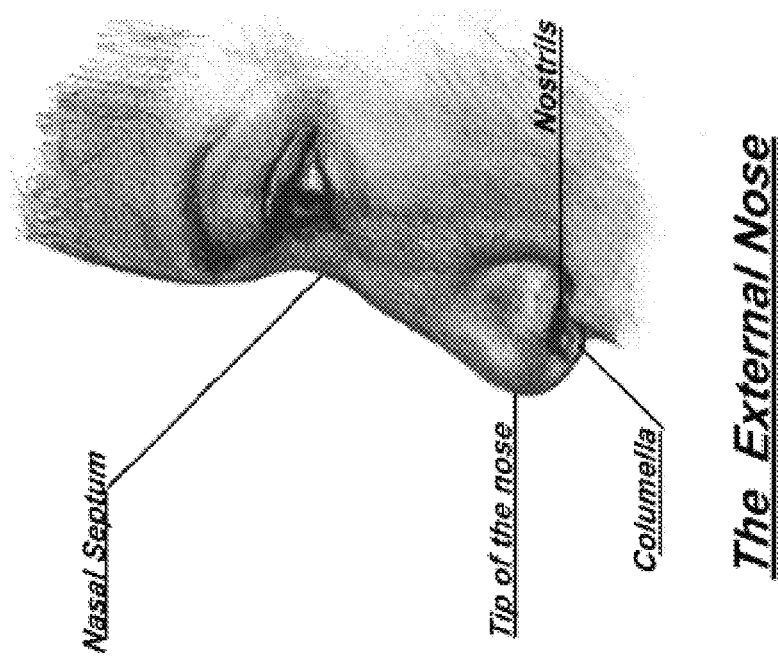
FIG. 1 is an illustration identifying the location of the nasal columella.

Provided according to some embodiments of the invention are photoplethysmography (PPG) sensors configured to obtain PPG signals from the nasal columella. As used herein, the "nasal columella" refers to the fleshy skin-covered tissue that is anterior to the cartilage of the nasal septum. This is shown in FIG. 1. The nasal columella has sometimes been referred to as part of the nasal septum, but the PPG probes known and used for nasal septum PPG use the cartilaginous portion of the nasal septum, which is covered with mucosal tissue. Thus, as used herein, the nasal columella only refers to the fleshy skin covered tissue that is anterior to the cartilage of the nasal septum.

In some embodiments, the PPG sensors include a sensor body, a structural support that is configured to secure to the nasal columella. In some embodiments, the sensor body is a clip body. The term "clip body" refers to a device that has at least two end portions that grasp and secure to a tissue site. While, in general, the PPG sensors include a clip body, it is not required. For example, a transmission or reflectance PPG sensor may be used and secured to the columella by some other fashion.

Thus, PPG sensors according to embodiments of the invention may be configured to clip and/or secure onto the nasal columella. The term "secure" means to attach sufficiently to the columella tissue to allow for a suitable PPG signal to be generated. In some cases, the sensor body is configured to secure onto the columella such that no additional support is necessary to allow for a suitable PPG signal to be reliably generated. However, in some cases, the sensor body may be secured with the aid of an external support, for example, an additional structural support, a wire or cord, or an adhesive product such as tape. Such supports may be desirable to stabilize the sensor to prevent against signal loss, for example, due to the patient's movement, or due to movement (e.g., jostling, pulling, pushing) of the sensor or a cable attached thereto.

The sensor body may be formed of any suitable material, including but not limited to, metals, polymers, polymer blends, and combinations thereof. Many thermoplastic and thermoset polymers may be suitable for use in the sensor body. However, in particular embodiments, the sensor body includes polycarbonate, acetal, nylon, polyester, or a combination thereof. Many metals may also be suitable for use in the sensor body, and in some embodiments, malleable metals, such aluminum or nitinol, may be desirable. In some embodiments, the sensor body is a molded article, such as a molded polymer article or a molded metallic article. In a particular embodiment, the material of the sensor body and/or clip is highly opaque and non-tranmissive of light in the visible and IR spectrums to prevent the light from an emitter from reaching the detector without first passing through tissue at the measurement site.

The sensor body may be composed of smaller pieces, which are assembled to form the sensor body, but in some embodiments, the sensor body is a single molded article. The use of a single molded article eliminates the need for assembly of the sensor or clip body, and so may increase manufacturing efficiency and/or decrease manufacturing costs. In some embodiments, a clip body may be flexible and/or malleable. In particular embodiments, the flexural modulus of the material that forms the clip body is in a range of 300,000 to 350,000 psi, and in some cases, in a range of 350,000 to 450,000 psi.

Figure 2A:
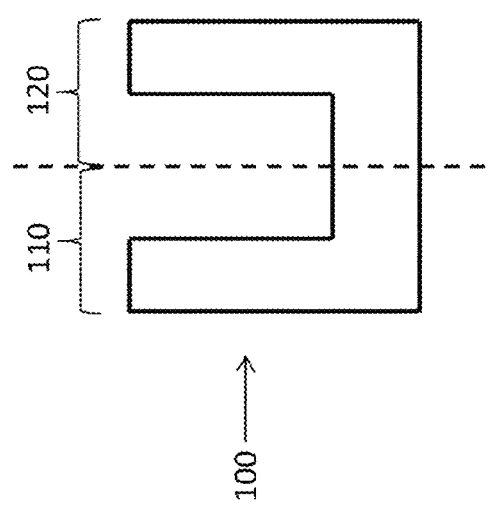
FIGS. 2A-2D are cross-sectional illustrations showing examples of different types of clip body configurations.
Figure 2B:
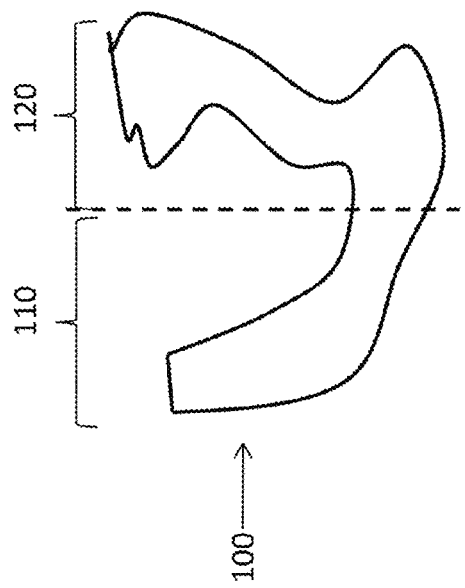

A clip body may be configured in a number of shapes, including, for example, "U-shaped" or "C-shaped", squared, rounded, pointed, regular or irregular shaped. FIGS. 2A-2D provide coarse cross-sectional illustrations of a type of clip body 100 that includes a first end portion 110 and a second end portion 120. As shown in FIG. 2A, the clip body 100 may be curved, but other configurations may be suitable or even desirable. As shown in FIG. 2B, in some embodiments, the clip body 100 may have a square or rectangular shape.

Figure 2C:
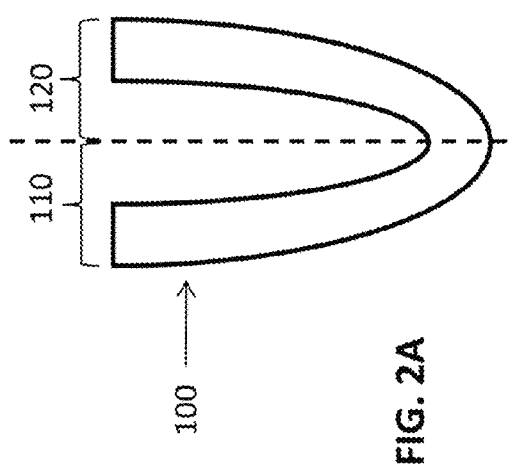
Figure 2D:
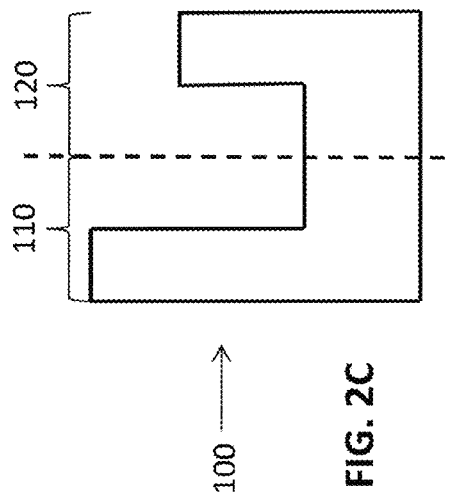

FIG. 2B also shows a first end portion 110 and a second end portion 120 that are the same or substantially the same length. However, in other embodiments, the end portions may be of different lengths and/or different shapes. FIG. 2C depicts a clip body 100 that has a first end portion 110 and a second end portion 120 having different lengths. In some embodiments, a first end portion 110 and/or a second end portion 120 of the clip body 100 may include a concave portion and/or convex portion (not shown). For example, in some cases, a first end portion 110 may be convex while a second end portion 120 may be concave. As shown in FIG. 2D, the clip body may also be irregularly shaped. In particular embodiments, the clip body 100 may be shaped to conform a curvature of the nasal columella. In some embodiments, a first end portion of the clip body is configured to secure to a portion of nasal columella tissue adjacent to a first nostril of an individual and a second end portion of the clip body is configured to secure to a portion of nasal columella tissue adjacent to a second nostril of the individual.

Although FIGS. 2A-2D show a particular boundary between the first and second end portions, such as halfway or at a "central point" between the two ends of the clip body, the exact location of the boundary is not critical. However, in general, a first end portion grasps one side of a tissue and a second end portion grasps the other side of the tissue. For example, in FIG. 2C, the end portions have two different lengths, but the clip body may be configured such that a longer end portion is meant to grasp one side of a tissue, while the shorter end is meant to grasp the other side of the tissue. As an additional example, for the irregular clip body 100 in FIG. 2D, while it is clear that there are two end portions, there is no clear central point. Thus, any and all reasonable apportionments of the first and second end portions of the clip body are envisioned.

FIGS. 3A and 3B also show additional irregular clip body styles, including those with a grips attached to the sensor, as shown in FIG. 3B. In FIG. 3A, the columella sensor 300 is shaped to conform to the curvature of the columella at the base 320 of the sensor body but becomes flared at the end portions, which may help in securing the sensor 300 to the columella. In this embodiment, the emitter(s)/detector pair 310 are positioned proximate to the base 320 of the columella sensor 300, so they are at substantially the beginning of the curvature extending from the base 320. For example, in some embodiments, the emitter(s) and detectors may be 2-8 mm, and in some cases 4-8 mm from the base 320. In FIG. 3B, the columella sensor 300 has an extended tip section 330 that may not contact the columella but may facilitate securing of the sensor. There may also be grips 340 attached to the extended tip portion 330 that when pressed together allow the clip body to open.

In some cases, there may be additional structural, functional or design elements in or on the clip/sensor body. For example, the clip body may have additional arms or extensions, and so may have additional end portions. The clip body may also be configured so that it can retract or extend to facilitate adjustment or placement of the sensor. The clip body may have apertures or other features such as, for example, those described in U.S. patent application Ser. No. 13/650,310, filed Oct. 10, 2012, entitled "Photoplethysmography Sensors," the entire contents of which are incorporated by reference herein.

Figures 4A, 4B:
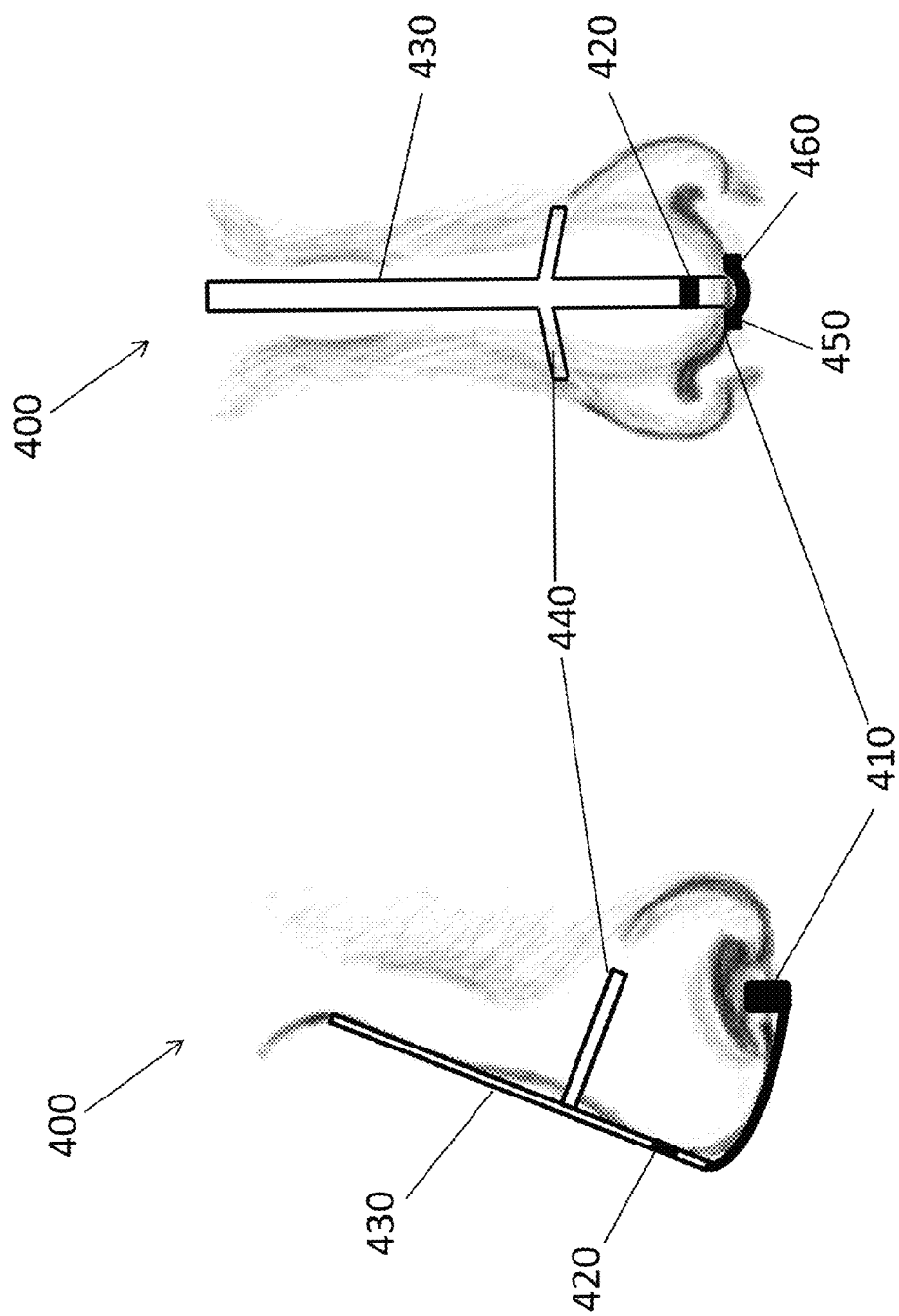
FIGS. 4A and 4B show a side view and a front view, respectively, of a columella sensor according to an embodiment of the invention.

In particular embodiments, the PPG sensors may include at least one emitter and at least one detector at the nasal columella and additional emitter(s) and/or detector(s) at a different (secondary) nasal location (e.g., tip of nose or nasal alar). Such embodiments may allow for the detection of differences in blood flow at different nasal locations. An example of such a sensor is shown in FIGS. 4A and 4B, which shows a sensor 400 that includes emitter(s) and detector(s) 410 at the nasal columella and an additional emitter(s) and/or detector(s) 420 at the tip of the nose. FIG. 4A shows a side view of the sensor 400, and shows that a cable such as a flex circuit 430 may be attached to the sensor at the tip of the nose, and additional taping or wings 440 may be provided to secure the sensor 400. FIG. 4B shows a front view of the same sensor. In this view, it can be seen that along with the emitters(s) and detector(s) 410 at the nasal columella, in this particular embodiment, the sensor 400 includes a first thermistor 450 configured to detect airflow from a first nostril and a second thermistor 460 configured to detect airflow from the second nostril. In some cases, light from an emitter at the columella may be detected by a detector at the secondary nasal location (in this case, the tip), and in some cases, light from an emitter at the secondary nasal location may be detected by a detector at the columella. In some cases, the secondary nasal location may include both an emitter and detector and thus operate independently of the emitter(s) and detector(s) at the columella.

In some embodiments, the clip body is relatively small because of the small amount of tissue at the nasal columella. Thus, in some embodiments, the clip body has a total length in a range of 20 to 30 mm. The total length refers to the distance between the two securing ends of the clip, as measured end to end along the length of the clip. The clip body may, in some cases, be relatively narrow so that the widest portion of the clip body is in a range of 4 to 6 mm, and in some cases, in a range of 2 to 4 mm. The size and shape of the nasal columella sensor may vary. In some embodiments, a single size and shape of nasal columella sensor may be used on all patients. However, in other embodiments, the sensor may be manufactured at different sizes and configurations to accommodate different types of patients, including children, young adults and adults, and to accommodate different nose sizes and shapes. This may affect the distance the sensor is inserted into the nostril.

In some cases, the intranasal portion of the sensor extends into the nostril a distance in a range of about 2 to about 8 mm, and in some embodiments, at a distance in a range of about 4 to 8 mm. In some cases, the intranasal portion of the sensor may be varied based on the type of patient (e.g., child vs. adult) and the size of the individual's nose.

One advantage of using a nasal columella PPG sensor is that it may be configured such that PPG sensors can be combined with other sensors to measure PPG signals and detect airflow, temperature, pressure or other respiratory parameters from both nostrils at the same time and with an array of sensors within a single device. Thus, the PPG sensors described herein may include at least one secondary respiration detector, and in some embodiments, two or more secondary respiration detectors. In some cases, the sensor may be configured such that a first secondary respiration detector detects airflow from a first nostril, and wherein a second secondary respiration detector detects airflow from a second nostril. As described below, examples of secondary respiration detectors include thermistors, thermocouples, RTDs, moisture detectors, capnometers, microphones, pressure sensors, nasal airway flow detectors, and vibration detectors.

Electronic components may be provided to the PPG sensors described herein by any suitable method. However, in particular embodiments, a flex circuit is used in combination with the clip body. The flex circuit may provide at least one electronic component to the sensor, and any suitable electronic component may be included in or on the flex circuit. When a flex circuit is said to "include" or "comprise" an electronic component, it is meant that the electronic component is within the flex circuit or on a surface of the flex circuit. In order to secure sufficiently to the tissue, the flex circuit may be attached or adjacent to the sensor body. The term "attached" includes mechanical attachment, e.g., via hooks or fasteners, or chemical attachment, e.g., via adhesives. The term "adjacent" means that the flex circuit is next to and/or touching the sensor body, but not actually attached to the clip body. As used herein, the term "joined" will refer to both attaching the flex circuit to the clip body and placing the flex circuit adjacent to the clip body. In some embodiments, one or more elastomeric sleeves sufficiently bind the sensor body and the flex circuit together so that the sensor body and the flex circuit need not be attached to each other. Thus, in some embodiments, no adhesive is present between the flex circuit and the clip body, between the clip body and the elastomeric sleeve and/or between the flex circuit and the elastomeric sleeve.

The PPG sensors, such as via the flex circuit, include one or more components that emit light, and such components will be referred to herein as "emitters." As used herein, the term "light" is used generically to refer to electromagnetic radiation, and so the term includes, for example, visible, infrared and ultraviolet radiation. Any suitable type of emitter may be used, but in some embodiments, the emitter is a light-emitting diode (LED). In particular embodiments, a first emitter on the flex circuit emits light at a first wavelength, and a second emitter on the flex circuit emits light at a second wavelength. For example, a sensor that may be used to measure blood oxygen saturation levels may include a first emitter that emits light in the visible range and a second emitter that emits light in the infrared range. In some cases, a single emitter may emit light at a first wavelength and a second wavelength. One or more photodetectors, also referred to as "detectors", are also included on the flex circuit. The detector is configured to detect light from an emitter, and this detected light generates a PPG signal. Any suitable photodetector may be used. However, examples of photodetectors include photodiodes, photoresistors, phototransistors, light to digital converters, and the like.

While any suitable type of flex circuit may be used, in some embodiments, the flex circuit is a single electrically conductive layer, housed in insulative plastic, which has all of the electronic components on the same side of the circuit. Furthermore, in particular embodiments, the flex circuit includes a moisture protective conformal coating.

Electronic components that provide additional physiological monitoring to the sensor may also be included on the flex circuit. As described above, in some embodiments, at least one secondary respiration detector may be included on the columella sensor, and examples of respiration detectors include thermistors, thermocouples, RTDs, moisture detectors, capnometers, microphones, pressure sensors, nasal airway flow detectors, and vibration detectors. Other physiological monitoring components that may be included in the columella sensors include oxygen sensors, pH sensors, and sensors for identifying and/or measuring particular compounds in the nasal airflow.

In some embodiments, an electronic component for wireless communication may be included in or on the columella sensor, such as via the flex circuit. Any suitable wireless communication component may be included on the flex circuit, but in some embodiments, a Bluetooth®, WiFi and/or infrared technology may be used. Such electronic components may communicate with a receiver apparatus so that PPG signals acquired by the sensor may be transmitted wirelessly to a control and/or signal processing unit.

When a flex circuit is used, the electronic component may be mounted on the flex circuit by any suitable technique, including, for example, via soldering and/or adhesives. The electronic components may also be mounted in any suitable configuration and on any part of the flex circuit or other part of the sensor. For example, in some cases, an emitter may be mounted on a first end portion of the flex circuit and the detector may be mounted on a second end portion of the flex circuit. Furthermore, in some embodiments, an emitter and a detector may be on the same end portion of the flex circuit, and in some cases, may be adjacent to each other. In some embodiments, the electronic components are "through-hole components" or "chip on board" components, so that the electronic components are not mounted on the surface of the flex circuit but are otherwise incorporated into the flex circuit. It is also to be understood that while the flex circuit is included to introduce electronic components to the sensor, in some embodiments, electronic components may also be present on other portions of the sensor, including the sensor body and/or the elastomeric sleeve.

In some embodiments, the PPG sensor (e.g., via the flex circuit) includes or is attached to a wire or cable for transmitting or communicating signals from the sensor to a computer or other analysis/processing equipment. In some cases, a portion of flex circuit itself may be considered part of the cabling. The flex circuit may also include a connector for coupling the flex circuit to a wire, cable or another electronic device. Any suitable wire, cable or other electrical connector may be used as the connector. In other embodiments of the invention, the PPG signals may be transmitted wirelessly, and so no wire or cabling is needed, and thus, the sensor may not include any cables or connectors.

In particular embodiments, the PPG sensors may include elastomeric sleeves. The "elastomeric sleeve" is an elastomeric material that envelops part of the sensor/clip body and part of the flex circuit attached or adjacent thereto. The sleeve may be formed from more than one piece of elastomeric material, but in some embodiments, the sleeve may be a molded elastomeric sleeve, and as such, the sleeve may be a single molded elastomeric article. Different types of elastomeric sleeves that may be used with the sensors described herein include those discussed in U.S. patent application Ser. No. 13/650,310, filed Oct. 10, 2012, entitled "Photoplethysmography Sensors," incorporated by reference herein.

According to some embodiments of the invention, the PPG sensor is partially or completely disposable. As such, the sensor may be used for a single use or for more than one use, for example, 2-10 uses, including 2, 3, 4 or 5 uses. In such cases, the sensor body, the flex circuit and the elastomeric sleeve may be formed from a sufficiently inexpensive material that also meets safety and performance standards. In addition, the relatively few assembly steps also decrease production costs and may allow for the partial or complete disposability of the sensor. The disposability of the sensor may be advantageous in some cases because it may decrease or eliminate the need for cleaning and disinfection, which may, in turn, improve the ease of use for medical personnel.

Any suitable method of making the PPG sensors described herein may be used. However, particular methods of making some types of PPG sensors are described in U.S. patent application Ser. No. 13/650,310, filed Oct. 10, 2012, entitled "Photoplethysmography Sensors," incorporated by reference in its entirety herein.

The nasal columella sensors, according to particular embodiments, may also include or be combined with a nasal cannula for delivery of breathing gases, such as oxygen or oxygen-enriched air. The nasal cannula may be incorporated into the nasal columella sensor in a number of different ways. For example, in some embodiments, the nasal cannula may be affixed or secured to the outside (or inside) of the sensor so that it is inserted into the nostril with the end portion of the sensor that secures inside the nasal cavity. As another example, in some cases, the clip body may have an aperture defined therein, so that the cannula may run through the clip body. In such case, any elastomeric sleeves may have an opening that allows the cannula to enter or exit the sensor. As an additional example, the cannula may run between clip body and flex circuit, and such a cannula could also enter and exit the sensor through openings in elastomeric sleeves.

Accessories for Use with Nasal Columella Sensors

Further provided according to some embodiments of the present invention are earpieces that are configured to direct the flex circuit and/or other cables behind the patient's ear and so lead them away from the patient's face. The earpiece may also be configured to couple with a flex circuit, connector portion or adaptor instead of merely guide the wires or cables behind the patient's ear. In some cases, a flex circuit may be configured to directly couple with the earpiece, with or without an adaptor, and in some cases, additional wires and connectors may be included between the flex circuit and the earpiece.

Also provided according to embodiments of the invention are sensor kits. Such kits may include a PPG sensor according to an embodiment of the invention, and an applicator configured to secure the sensor to the nasal columella. In some embodiments, the kit may include other accessories, such as an earloop, tape and/or cleaning products. The kit may also allow for the columella sensor, applicator, and any other accessories, to be contained within sterile packaging. The packaging, once opened, may provide a sterile sensor and applicator, and in some cases, the applicator may already be joined or attached to the sensor so that the sensor can be immediately placed on a patient. Once placed on the patient, the applicator may then be removed. Furthermore, in some embodiments, the sensor and/or applicator may be disposable so that it can be discarded after use.

Systems and Methods for Using Nasal Columella Sensors

The nasal columella sensors described herein may be used in any suitable fashion, and with any suitable signal processing apparatus or method. Thus, in some embodiments, provided are systems that include at least one nasal columella sensor according to an embodiment of the invention. Such systems may also include a processing apparatus, such as a computer or other analytical equipment, that is communicatingly connected to the nasal columella sensor. Examples of systems and methods that may be used in combination with the nasal columella sensors described herein may be found in U.S. Pat. No. 6,909,912, U.S. Pat. No. 7,127,278, U.S. Pat. No. 7,024,235, U.S. Pat. No. 7,785,262, U.S. Pat. No. 7,887,502, U.S. Publication No. 2008/0058621, U.S. Publication No. 2008/0190430, U.S. Publication No. 2010/0192952, PCT Application No. PCT/US2011/048083 and PCT/US2011/046943, the contents of each of which are incorporated herein by reference in their entirety.

The nasal columella sensors may be secured to the patient in any suitable manner. For example, once the nasal columella sensor is placed onto a subject, the connector/adapter may be connected to a signal processing apparatus, and signals can be generated. In embodiments wherein a wireless sensor is used, no connection of wires or cables may be necessary for use. In some cases, the sensor may be additionally secured by taping the sensor, flex circuit and/or any additional cabling. As described above, this may ensure that the sensor remains in place despite patient movement or jostling of the sensor or cables, for example, by medical personnel. In some cases, a lubricant may be applied to the nasal columella sensor or the skin/mucosa to which it is to be applied to improve signal and/or to properly situate the sensor. In such cases, taping of the sensor and/or cables may also aid in securing the sensor to the patient.

As described above, nasal columella sensors may be used for determining respiration rate and/or other respiratory parameters and conditions. As such, the nasal columella PPG sensor may be used as a respiration detector. In some embodiments, the nasal columella sensors described herein may be useful with a secondary respiration detector as well, either as part of the sensor or as a separate device, to monitor respiration in a patient. The data from two or more different respiration detectors may be compared, including in real time, which may provide additional information and/or enhanced confidence of the determination of respiratory parameters. As described elsewhere herein, secondary respiration detectors include, but are not limited to, thermistors, thermocouples, RTDs, moisture detectors, capnometers, microphones, pressure sensors, nasal airway flow detectors, such as nasal flow transducers, NAP, and via detectors of vibrations in the ear.

The nasal columella sensors described herein may be used in combination with other physiological monitors as well, either as part of the sensor, if applicable, or as a separate device. Examples include oxygen sensors, pH sensors, blood pressure monitors, breath constituent monitors, blood constituent monitors, heart rate monitors and depth of anesthesia monitors.

The nasal columella sensors described herein may also be used in combination with other PPG sensors, including those designed for emplacement at the nose (e.g., nasal alar, nasal septum and bridge of the nose), lip, cheek, tongue or a selected site at the ear (e.g., ear canal, concha, pinnae, scaphoid fossa, or ear lobe), forehead, fingers and toes. Description of monitoring two or more different sites on the body can be found, for example, in U.S. Pat. No. 6,909,912, which is incorporated herein by reference in its entirety. In particular embodiments, a nasal columella sensor described herein may be used with a sensor designed for emplacement at or on the ear. Particular examples of such ear PPG probes can be found in U.S. Pat. Nos. 7,341,559; 5,551,432 and 5,673,692, and in U.S. Patent Publication Nos. 2010/0217103, 2010/0049017, 2010/0331631 and 2009/0275813, the contents of each of which is incorporated herein by reference in its entirety for this purpose. In some cases, it may be useful to place a PPG sensor at a nasal columella site and at an ear site due to the differences in blood flow at the two different sites.

In some embodiments of the present invention, a nasal columella sensor may be included in a system that provides patient feedback when certain PPG signals or certain PPG signal levels are generated. For example, when the sensor is used for respiration monitoring, the PPG sensor may be used with a system that can alert the patient when respiration appears to be irregular or depressed. In particular embodiments, once the PPG signals from the sensor indicate troubled or depressed respiration, the PPG signal processing unit communicates with a device that alerts the patient, e.g., by applying a wisp of air on the cheek (malar region) to stimulate respiration. Other methods of stimulating respiration include tickling the malar region, and application of heat, cold and/or mild electrical stimulation. In some cases, the nasal columella sensors themselves may include a mechanism for alerting the patient. For example, the nasal columella sensor might include a component that provides a wisp of air to the patient's cheek or may provide mild electrical stimulation. In some embodiments, the system may also be configured to alert medical personnel or to take another appropriate action (such as reduction in opiate administration or increased supply of air to an intubated subject), at the time the stimulus is applied and/or when the stimulus does not restore the patient's breathing to acceptable levels.

In the drawings and specification, there have been disclosed embodiments of the invention and, although specific terms are employed, they are used in a generic and descriptive sense only and not for purposes of limitation, the scope of the invention being set forth in the following claims.

We claim:

1. A method of obtaining a photoplethysmography (PPG) signal, comprising:
   securing a PPG sensor onto a nasal columella of an individual; and
   obtaining a PPG signal from the PPG sensor, wherein the PPG sensor is configured such that an emitter on the PPG sensor emits radiation through a portion of the nasal columella and a detector on the PPG sensor detects light transmitted through or reflected by the portion of the nasal columella.

2. The method of claim 1, wherein the PPG sensor comprises a secondary respiration detector.

3. The method of claim 2, wherein the PPG sensor comprises two secondary respiration detectors.

4. The method of claim 3, wherein a first secondary respiration detector is configured to detect airflow from a first nostril, and wherein a second secondary respiration detector is configured to detect airflow from a second nostril.

5. The method of claim 2, wherein the secondary respiration detector comprises a thermistor.

6. The method of claim 2, wherein the secondary respiration detector comprises a capnometer.

7. The method of claim 1, wherein the PPG sensor comprises a flexible molded polymeric clip body.

8. The method of claim 7, wherein a first end portion of the polymeric clip body secures to a first portion of nasal columella tissue and a second end portion of the polymeric clip body secures to a second end portion of nasal columella tissue.

9. The method of claim 7, wherein the clip body generally conforms to the curvature of the nasal columella.

10. A photoplethysmography (PPG) sensor comprising a clip body configured to secure to the nasal columella, wherein the clip body is configured to extend into the nostril a distance in a range of 4 to 8 mm.

11. The PPG sensor of claim 10, wherein a surface of the clip body is shaped to conform to a curvature of the nasal columella.

12. The PPG sensor of claim 10, further comprising a secondary respiration detector.

13. The PPG sensor of claim 12, wherein the secondary respiration detector comprises a thermistor.

14. The PPG sensor of claim 10, further comprising at least two secondary respiration detectors.

15. The PPG sensor of claim 14, wherein a first secondary respiration detector is positioned on the sensor such that it is exposed to airflow from a first nostril and a second secondary respiration detector is positioned on the sensor such that it is exposed to airflow from a second nostril.

16. The PPG sensor of claim 10, wherein a first end portion of the clip body secures to a portion of nasal columella tissue adjacent to a first nostril of an individual and a second end portion of the clip body secures to a portion of nasal columella tissue adjacent to a second nostril of the individual.

17. The PPG sensor of claim 10, wherein the sensor comprises:
   (a) a clip body comprising a first end portion and a second end portion;
   (b) a flex circuit attached or adjacent to the clip body, wherein the flex circuit comprises an emitter and a detector; and
   (c) an elastomeric sleeve that envelops (1) at least part of the first end portion and at least part of the flex circuit attached or adjacent thereto; or (2) at least part of the second end portion and at least part of the flex circuit attached or adjacent thereto.

18. The PPG sensor of claim 17, wherein the elastomeric sleeve compressively envelops (1) the at least part of the first end portion and the at least part of the flex circuit attached or adjacent thereto; or (2) the at least part of the second end portion and the at least part of the flex circuit attached or adjacent thereto.

19. The PPG sensor of claim 18, wherein no adhesive is present between the clip body and the flex circuit, between the clip body and the elastomeric sleeve or between the flex circuit and the elastomeric sleeve.

20. The PPG sensor of claim 10, wherein the clip body is a flexible molded polymer clip.

21. A system for monitoring a subject, comprising the PPG sensor of claim 10; and a computer communicatingly connected to the PPG sensor.

22. The system of claim 21, wherein the computer comprises a processing module configured to process PPG signals from the PPG sensor to determine the respiratory rate of the subject.

23. The system of claim 21, wherein the computer comprises a processing module configured to process PPG signals from the PPG sensor to monitor blood flow in the subject.

24. A photoplethysmography (PPG) sensor comprising (1) a clip body configured to secure and obtain photoplethysmography signals from tissue at the nasal columella and (2) an extended sensor portion configured to secure and obtain photoplethysmography signals from tissue at a secondary nasal location.

25. The PPG sensor of claim 24, wherein the secondary nasal location is the tip of the nose.

26. A method of obtaining a photoplethysmography (PPG) signal, comprising:
   securing the PPG sensor of claim 24 onto an individual; and obtaining a PPG signal from at least one detector positioned at the columella and/or at least one detector positioned at the secondary nasal location.

* * * * *